(12) United States Patent
Urich et al.

(10) Patent No.: US 6,425,883 B1
(45) Date of Patent: Jul. 30, 2002

(54) METHOD AND APPARATUS FOR CONTROLLING VACUUM AS A FUNCTION OF ULTRASONIC POWER IN AN OPHTHALMIC PHACO ASPIRATOR

(75) Inventors: Alex Urich, Mission Viejo; Michael Curtis, Lake Forest, both of CA (US)

(73) Assignee: Circuit Tree Medical, Inc., Mission Viejo, CA (US)

(*) Notice: Subject to any disclaimer, the term of this patent is extended or adjusted under 35 U.S.C. 154(b) by 0 days.

(21) Appl. No.: 09/372,476

(22) Filed: Aug. 11, 1999

Related U.S. Application Data

(63) Continuation-in-part of application No. 09/097,099, filed on Jun. 16, 1998, now abandoned.
(60) Provisional application No. 60/084,852, filed on May 8, 1998.

(51) Int. Cl.[7] .................................................. A61M 1/00
(52) U.S. Cl. .................. 604/119; 604/118; 604/30; 604/35; 604/22
(58) Field of Search .............................. 604/30, 31, 35, 604/33, 118, 119, 22; 128/748, 645, 675, 676; 606/1, 107, 166

(56) References Cited

U.S. PATENT DOCUMENTS

| | | |
|---|---|---|
| 1,206,126 A | 11/1916 | Mitsch |
| 3,301,063 A | 1/1967 | Kisling III, et al. |
| 3,476,144 A | 11/1969 | Krantz |
| 3,501,959 A | 3/1970 | Womack |
| 3,661,144 A | 5/1972 | Jensen et al. |
| 3,784,039 A | 1/1974 | Marco |
| 3,812,855 A | 5/1974 | Banko |
| 3,863,504 A | 2/1975 | Borsanyi |
| 4,016,882 A | 4/1977 | Broadwin et al. |
| 4,226,124 A | 10/1980 | Kersten |
| 4,382,442 A | 5/1983 | Jones |
| 4,425,115 A | 1/1984 | Wuchinich |
| 4,457,455 A | 7/1984 | Meshberg |
| 4,465,470 A | 8/1984 | Kelman |
| 4,468,217 A | 8/1984 | Kuzmick et al. |
| 4,526,593 A | 7/1985 | Meyerson |
| 4,650,461 A | 3/1987 | Woods |
| 4,722,350 A | * 2/1988 | Armeniades et al. ....... 128/748 |
| 4,770,654 A | * 9/1988 | Rogers et al. ................ 604/22 |
| 4,808,154 A | 2/1989 | Freeman |
| 4,832,685 A | 5/1989 | Haines |

(List continued on next page.)

FOREIGN PATENT DOCUMENTS

| | | |
|---|---|---|
| EP | 0 251 694 B1 | 7/1988 |
| EP | 0 251 694 A2 | 7/1988 |
| EP | 0 284 322 A3 | 9/1988 |
| EP | 0 284 322 A2 | 9/1988 |
| EP | 0 284 322 B1 | 2/1993 |
| EP | 0 931 519 A1 | 7/1999 |
| WO | WO 88/10102 | 12/1988 |

Primary Examiner—Brian L. Casler
Assistant Examiner—Jennifer Maynard
(74) Attorney, Agent, or Firm—Irell & Manella, LLP

(57) ABSTRACT

An aspiration system that may include a control valve to allow a flow of fluid into an aspiration line and vary a vacuum pressure within the line. The system may include a pressure transducer that is coupled to the aspiration line by a sensor line and a check valve. The check valve prevents a back flow of fluid from the aspiration line to the pressure line. The system may further have a control circuit that is coupled to the pressure transducer and the control valve. The control circuit may control the control valve and regulate the vacuum pressure within the aspiration line. The control circuit may receive an input signal that also controls a medical handpiece. The input signal can be generated by a foot pedal that also controls the handpiece. The system may thus have one foot pedal that can control the handpiece and the vacuum pressure of the aspiration line.

17 Claims, 2 Drawing Sheets

U.S. PATENT DOCUMENTS

| | | |
|---|---|---|
| 4,838,853 A | 6/1989 | Parisi |
| 4,935,005 A | 6/1990 | Haines |
| 4,983,160 A | 1/1991 | Steppe et al. |
| 5,111,971 A | 5/1992 | Winer |
| 5,123,903 A | 6/1992 | Quaid et al. |
| 5,152,746 A | 10/1992 | Atkinson et al. |
| 5,167,725 A | 12/1992 | Clark et al. |
| 5,188,102 A | 2/1993 | Idemoto et al. |
| 5,197,485 A | 3/1993 | Grooters |
| 5,282,786 A | 2/1994 | Ureche |
| 5,312,329 A | 5/1994 | Beaty et al. |
| 5,324,297 A | 6/1994 | Hood et al. |
| 5,324,299 A | 6/1994 | Davison et al. |
| 5,342,380 A | 8/1994 | Hood |
| 5,354,265 A | 10/1994 | Mackool |
| 5,354,268 A | 10/1994 | Peterson et al. |
| 5,380,274 A | 1/1995 | Nita |
| 5,391,144 A * | 2/1995 | Sakurai et al. ................ 604/22 |
| 5,413,578 A | 5/1995 | Zahedi |
| 5,454,784 A | 10/1995 | Atkinson et al. |
| 5,464,389 A | 11/1995 | Stahl |
| 5,520,652 A | 5/1996 | Peterson |
| 5,582,588 A | 12/1996 | Sakurai et al. |
| 5,591,127 A | 1/1997 | Barwick, Jr. et al. |
| 5,628,743 A | 5/1997 | Cimino |
| 5,630,939 A | 5/1997 | Bulard et al. |
| 5,676,650 A | 10/1997 | Grieshaber et al. |
| 5,685,840 A * | 11/1997 | Schechter et al. ............ 604/22 |
| 5,700,240 A | 12/1997 | Barwick, Jr. et al. |
| 5,722,945 A | 3/1998 | Anis et al. |
| 5,730,156 A | 3/1998 | Mackool |
| 5,733,256 A | 3/1998 | Costin |
| 5,743,871 A | 4/1998 | Strukel et al. |
| 5,746,719 A | 5/1998 | Farra et al. |
| 5,766,146 A | 6/1998 | Barwick, Jr. |
| 5,807,310 A | 9/1998 | Hood |
| 5,810,765 A | 9/1998 | Oda |
| 5,817,099 A | 10/1998 | Skolik et al. |
| 5,843,021 A | 12/1998 | Edwards et al. |
| 5,890,516 A | 4/1999 | Talamonti |
| 5,897,569 A | 4/1999 | Kellogg et al. |
| 6,083,193 A | 7/2000 | Kadziauskas et al. |
| 6,110,259 A | 8/2000 | Shultz et al. |
| 6,179,803 B1 | 1/2001 | Edwards et al. |
| 6,193,683 B1 | 2/2001 | Ludin et al. |
| 6,203,540 B1 | 3/2001 | Weber |

\* cited by examiner

METHOD AND APPARATUS FOR CONTROLLING VACUUM AS A FUNCTION OF ULTRASONIC POWER IN AN OPHTHALMIC PHACO ASPIRATOR

CROSS-REFERENCE TO RELATED APPLICATIONS

This application is a continuation-in-part of application Ser. No. 09/097,099, Jun. 16, 1998, now abandoned.

This application claims benefit of Provisional Application 60/084,852 filed May 8, 1998.

BACKGROUND OF THE INVENTION

1. Field of the Invention

The present invention relates to a power source for an ultrasonically driven surgical handpiece.

2. Background Information

The lens of a human eye may develop a cataracteous condition which affects a patients vision. Cataracteous lenses are sometimes removed and replaced in a procedure commonly referred to as phacoemulsification. Phaco procedures are typically performed with an ultrasonically driven handpiece which is used to break the lens. The broken lens is removed through an aspiration line that is coupled to the handpiece. The aspiration line is connected to a pump which creates a vacuum pressure within the line.

The handpiece has a tip which is inserted through an incision in the cornea. The handpiece typically contains a number of ultrasonic transducers which convert electrical power into a mechanical oscillating movement of the tip. The distal end of the tip has an opening which is in fluid communication with the aspiration line. The oscillating movement of the tip breaks the lens into small pieces that are then drawn into the aspiration line through the tip opening.

The handpiece is connected to a console that contains a power source which drives the ultrasonic transducers. The power provided to the transducers can be controlled by the surgeon through a foot pedal that is connected to the console. During a phaco procedure a piece of the broken lens may be too large to be drawn through the tip. Such a condition may create an occlusion at the tip opening. The surgeon can further break up the piece by depressing the foot pedal and increasing the power to the transducers.

The tip occlusion reduces the vacuum pressure within the aspiration line downstream from the cornea. When the occlusion is removed there is a sudden change in pressure within the cornea. The sudden change in pressure may collapse the cornea. The surgeon must perform the procedure with skill to insure that this event does not occur.

U.S. Pat. No. 5,591,127 issued to Barwick Jr. et al. discloses a phaco system that senses the vacuum pressure within the aspiration line and varies the speed of the pump when the line pressure falls below a threshold vacuum level. The reduction in pump speed lowers the rate at which the vacuum pressure decreases while the aspiration line is occluded. Because of mechanical and pneumatic inertia, there is typically a time delay between when the vacuum pressure falls below the threshold value and when the reduced pump speed lowers the vacuum pressure. This time delay may allow an undesirable increase in the vacuum pressure of the aspiration line.

U.S. Pat. No. 4,395,258 issued to Wang et al. discloses an aspiration system that contains a pair of electronically controlled valves to control the vacuum pressure within an aspiration line. One of the valves controls the flow between the aspiration line and a vacuum pump. The other valve controls the flow of air from the atmosphere into the aspiration line. The valves are switched between open and closed positions by a controller that receives a feedback signal from a pressure transducer. The pressure transducer senses the vacuum pressure within the aspiration line.

The controller receives an input signal from a foot pedal that can be depressed by the surgeon. The controller compares the feedback signal from the pressure transducer with the input signal from the foot pedal. The controller can open and/or close either control valve based on the comparision between the two input signals. When used with an ultrasonically driven handpiece the Wang system requires two foot pedals. One foot pedal for the handpiece and another foot pedal for the aspiration system. It would be desirable to provide an ultrasonically driven handpiece/aspiration system that has only one foot pedal and automatically controls the vacuum pressure of the aspiration line.

The pressure transducer is typically in fluid communication with the aspiration line. After each procedure the transducer must be disconnected from the aspiration line and sterilized. Such a procedure takes time. Additionally, the sterilization process may degrade the pressure sensor. It would be desirable to provide a non-invasive pressure transducer assembly for an aspiration system.

SUMMARY OF THE INVENTION

One embodiment of the present invention is an aspiration system that may include a control valve to allow a flow of fluid into an aspiration line and vary a vacuum pressure within the line. The system may include a pressure transducer that is coupled to the aspiration line by a sensor line and a check valve. The check valve prevents a back flow of fluid from the aspiration line to the pressure line. The system may further have a control circuit that is coupled to the pressure transducer and the control valve. The control circuit may control the control valve and regulate the vacuum pressure within the aspiration line. The control circuit may receive an input signal that also controls a medical handpiece.

DETAILED DESCRIPTION OF THE INVENTION

One embodiment of the present invention is an ultrasonic surgical system which has a feedback loop that varies a power provided to an ultrasonically driven handpiece in response to a change in vacuum pressure within an aspiration line. The system includes a pressure sensor which can sense the vacuum pressure within the aspiration line. The ultrasonically driven handpiece is driven by a power source that is also connected to the pressure sensor. The power source varies the power output of the handpiece in response to changes in the vacuum pressure in a continuous non-step manner.

By way of example, the output power of the handpiece is increased when there is a reduction in the vacuum pressure. The variation in power may be a linear function of the change in vacuum pressure, so that the power continuously increases or decreases with a corresponding reduction or increase in vacuum pressure, respectively. Increasing the power in response to a reduction in line pressure may provide an automatic means for breaking tip occlusions. The continuous power response can provide a technique which has a lower average power than systems in the prior art. The lower power minimizes the amount of heat generated by friction between a cornea and a vibrating tip of the handpiece.

Figure 1:
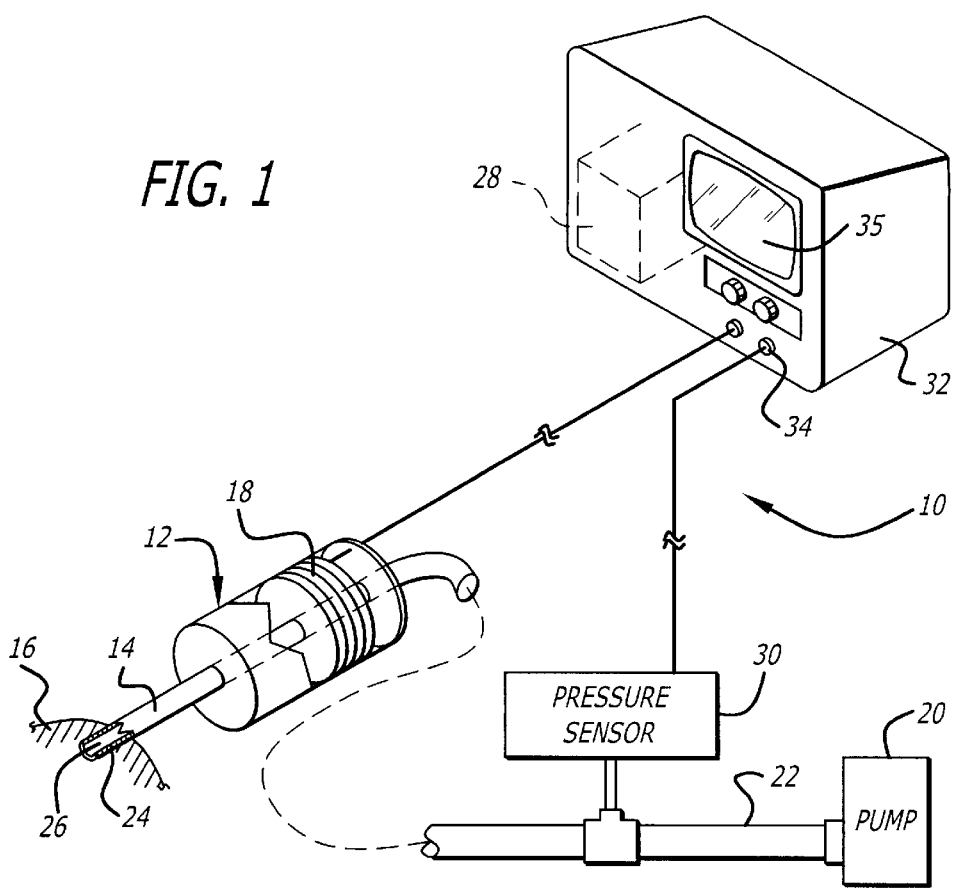
FIG. 1 is a schematic of an embodiment of an ultrasonic surgical system of the present invention.

Referring to the drawings more particularly by reference numbers, FIG. 1 shows an embodiment of an ultrasonic surgical system 10 of the present invention. The system 10 may include an ultrasonically driven handpiece 12 which has a tip 14 that can be inserted into a cornea 16. The handpiece 12 may include one or more ultrasonic transducers 18 which convert electrical power into mechanical movement of the tip 14. The handpiece 12 is typically held by a surgeon who performs a surgical procedure with the system 10. By way of example, the system 10 can be used to perform a phacoemulsification procedure to break and aspirate a lens of the cornea 16.

The handpiece 14 is coupled to a pump 20 by an aspiration line 22. The pump 20 creates a vacuum pressure within the aspiration line 22. The aspiration line 22 is in fluid communication with an inner channel 24 and opening 26 in the tip 14. The vacuum pressure within the line 22 can aspirate matter from the cornea 16.

The system 10 may include a power source 28 which provides electrical power to the transducers 18. The power source 28 may be connected to a pressure sensor 30 that senses the level of the vacuum pressure within the aspiration line 22. The power source 28 varies the output power of the transducers 18 in response to changes in the vacuum pressure within the line 22. In general, the power source 28 increases the output power of the transducers 18 when the vacuum pressure falls (eg. becomes more negative) and decreases the output power when the line pressure increases.

The power source 28 may be located within a console 32 that is connected to the sensor 30 and handpiece 12. The console 32 may have input knobs or buttons 34 which allow the surgeon to vary different parameters of the system 10. The console 32 may also have a readout display(s) 35 which provides an indication of the vacuum pressure, power level, etc. of the system 10.

Figure 2:
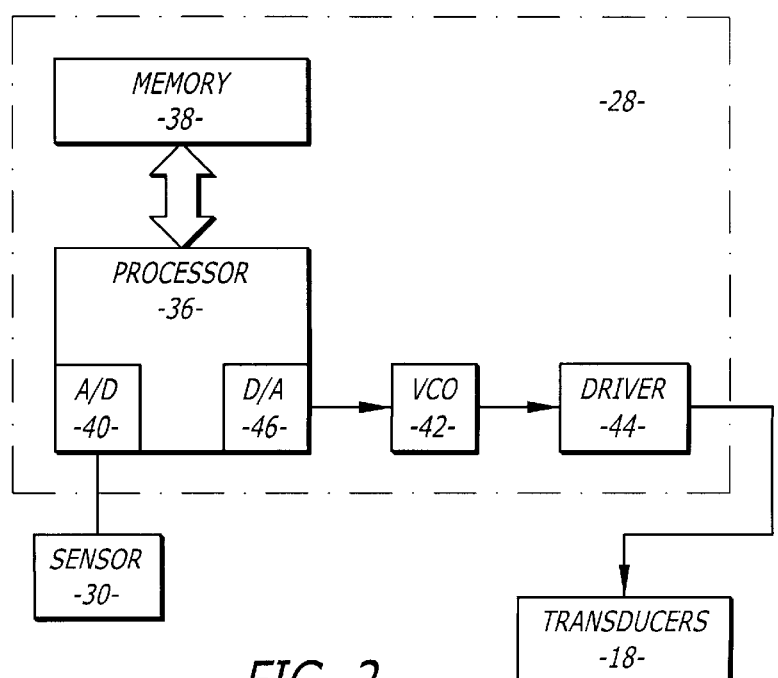
FIG. 2 is a schematic of a power source of the system.

FIG. 2 shows an embodiment of the power source 28. The power source 28 may include a microprocessor 36 that varies the output power of the transducers 18 in accordance with a software routine(s). The processor 36 can be connected to a memory device(s) 38 which contains instructions and data used to perform the software routine.

The processor 36 may be connected to the pressure sensor 30 which provides a signal that may vary in amplitude with changes in the line pressure. The signal may be converted to a digital bit string(s) by an analog to digital (A/D) converter 40.

The output of the processor 36 may be connected to a voltage controlled oscillator (VCO) 42. The output of the VCO 42 may be a time varying analog signal which is amplified by a driver circuit 44 and provided to the transducers 18. By way of example, the output signal of the VCO 42 may be a series of square wave pulse. The frequency of the VCO output signal may vary with a corresponding change in the amplitude of the VCO input signal from the processor 36. The processor 36 may have a digital to analog (D/A) converter 46 to convert a digital bit string(s) to an analog VCO input signal. Although a processor 36 is shown and described, it is to be understood that the output of the transducer 18 can be connected directly to the input of the VCO 42.

The output of the power source 28 may be normally set at a frequency that is greater than the natural resonant frequency of the transducers 18. The output power of the handpiece 12 can be increased by decreasing the frequency of the output signal provided to the transducers 18. The lower frequency is closer to the natural frequency of the transducers 18. The transfer function of the transducers 18 increases as the input frequency approaches the natural frequency. Conversely, the power output of the transducers 18 decreases with an increase in the frequency of the VCO output signal. The variation in frequency may occur while the voltage of the VCO output signal remains at a constant valve.

The software routine performed by the microprocessor 36 can have an upper CEILING power limit and a lower IDLE power limit for the handpiece 12. The CEILING and IDLE limits can be varied by the surgeon through the input buttons 34. The IDLE power limit may be a minimum output power of the transducers 18 when there is a zero vacuum pressure within the aspiration line 22. The CEILING power limit may be a maximum output power of the transducers 18. The processor 36 may have an automatic scaling function which sets a power scale between the IDLE and CEILING limits based on the value of the CEILING limit set by the surgeon. The scale may be linear so that there is a linear correspondence between the vacuum pressure and the output power of the transducers 18.

The processor 36 may have a timer function which automatically reduces the CEILING limit to the IDLE limit if the system 10 is in the CEILING mode for a predetermined time interval. The processor 36 may have a counter which counts each time the system enters the CEILING mode. If the timer times out, the processor 36 places the system in the IDLE mode. The timer prevents the system from staying indefinitely in the high powered CEILING mode. The time interval can be set by the surgeon through the input buttons 34.

The processor 36 may also implement a delay function so that there is a time delay between a variation in the vacuum pressure and the change in the transducer power. The time delay may be implemented as a gradual variation in transducer power over time for each change in vacuum pressure. The time delay may be selectable and variable so that the surgeon can vary a delay slope defined by the change in transducer power versus a variation in the vacuum pressure. The delay function prevents instantaneous feedback which can create an unstable system.

In operation, a surgeon may insert the tip 14 into a cornea 16 to break and aspirate a lens. The vibratory movement of the tip 14 can break the lens into pieces which are then aspirated through the line 22. An occlusion at the tip opening 26 will lower the pressure within the aspiration line 22. The lower line pressure is sensed by the sensor 30 and will cause the processor 36 to increase the power output of the transducers 18. The increase in transducer power may assist in breaking the occlusion.

An occlusion may occur with the line 22. Such an event may cause the system to enter the CEILING mode. If the occlusion remains in the line 22 for a predetermined time interval the processor 36 may reduce the transducer power to the IDLE mode.

Figure 3:
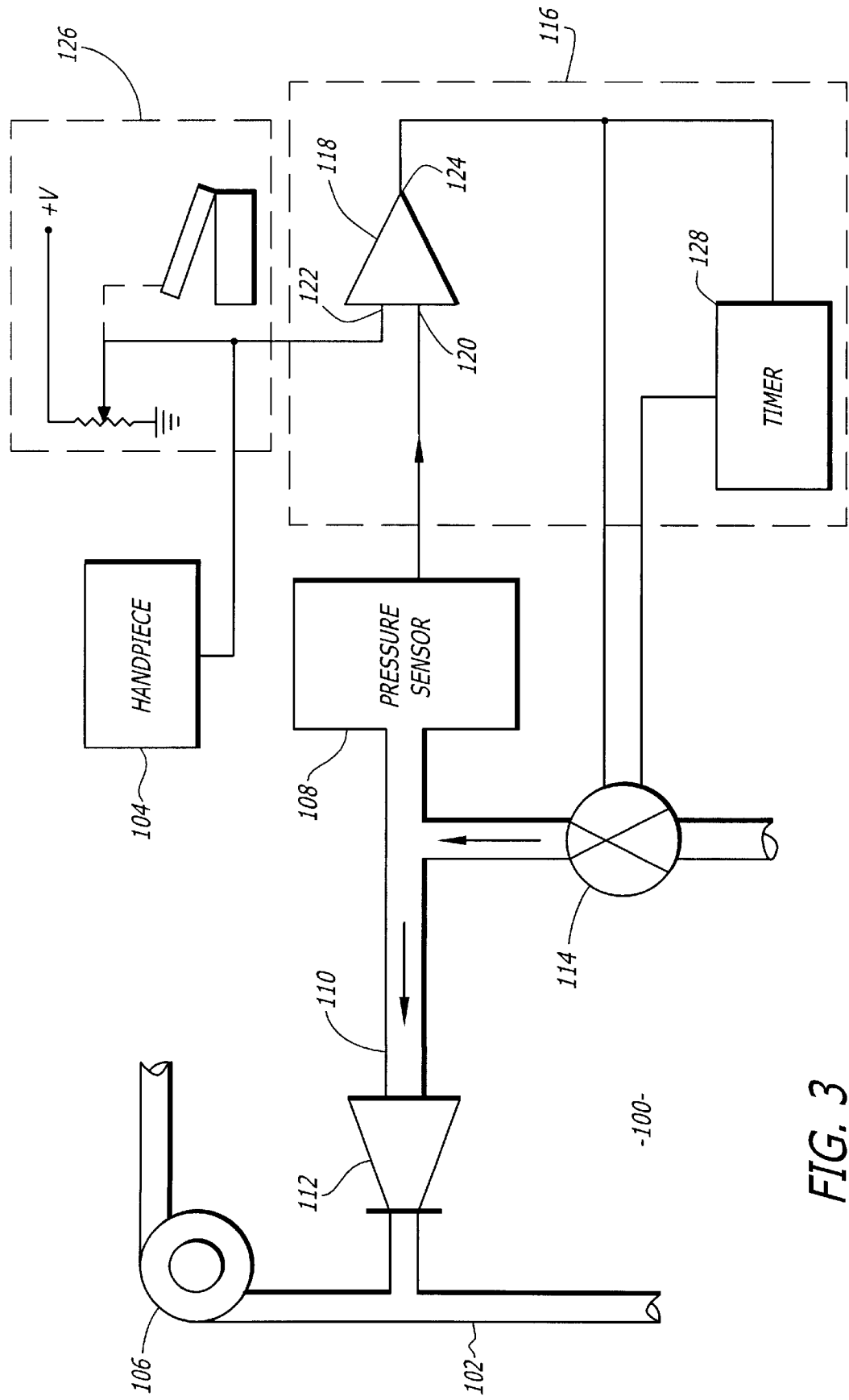
FIG. 3 is a schematic of an alternate embodiment of an aspiration system.

FIG. 3 shows an alternate embodiment of an aspiration system 100 that can automatically control the vacuum pressure within an aspiration line 102. The apsiration line 102 may be connected to a handpiece 104. The handpiece 104 may be the same or similar to the device shown in FIG. 1 and described above. The aspiration line 102 may provide a conduit between the handpiece 104 and a pump 106. The pump 106 may create a vacuum pressure in the line 102 that pulls fluid and debris from the handpiece 104. By way of example, the pump 106 may be a non-invasive peristaltic pump unit.

The aspiration system 100 may further have a pressure sensor 108 that is coupled to the aspiration line 102 by a sensor line 110 and a one-way check valve 112. The one-way check valve 112 will allow fluid to flow from the sensor line 110 to the aspiration line 102, but will not allow fluid to flow from the aspiration line 102 to the sensor line 110. The oneway check valve 112 essentially seals the pressure sensor 108 from the aspiration line. With such an arrangement the pressure sensor 108 does not have to be sterilized after each surgical procedure.

The system 100 may further have a control valve 114 that can be switched between a closed position and an open position. In the open position the control valve 114 allows a positive pressure fluid to flow into the sensor line 110. The pressure of the fluid within the sensor line 110 is greater than the vacuum pressure within the aspiration line 102. The differential pressure between the fluid within the sensor line 110 and the vacuum pressure within the aspiration line 102 opens the check valve 112. The opened check valve allows the fluid within the sensor line 110 to flow into the aspiration line 102 and increase the vacuum pressure within the line 102. The control valve 114 can be connected to atmosphere, a tank of fluid, or other source of positive pressure.

The aspiration system 100 may include a control circuit 116 that can switch the control valve 114 and regulate the vacuum pressure within the aspiration line 102. The control circuit 116 may include a comparator 118 that has a first input 120 which receives a sensor output signal from the pressure sensor 108 and a second input 122 that receives a threshold voltage signal. The comparator 118 has an output 124 that provides a control output signal to the control valve 114. The control output signal switches the control valve 114 from the closed position to the open position to allow fluid to flow into the aspiration line 102 through the check valve 112.

The second input 122 of the comparator 118 may be connected to an input device such as a foot pedal 126. The foot pedal 126 can be depressed by the surgeon to vary the amplitude of the threshold voltage signal. The threshold voltage signal can also be used to control the power of the handpiece 104. Although a direct connection to the foot pedal 126 is shown and described, it is to be understood that the second input 122 may be connected to a microprocessor. The microprocessor may also provide the function of the comparator 118 and generate the output signal that switches the control valve 114.

In operation, the surgeon can depress the foot pedal to power the handpiece 104. Depressing the foot pedal also sets the threshold voltage provided to the comparator 118. The pressure transducer 108 provides a sensor output signal that corresponds to the pressure within the sensor line 110. In a steady state condition the pressure within the sensor line 110 is approximately equal to the vacuum pressure within the aspiration line 102.

An occlusion will cause a reduction in the pressure within the aspiration line 102. The decrease in pressure within the aspiration line 102 creates a pressure differential that opens the check valve 112 and allows fluid to flow from the sensor line 110 and reduce the pressure in the line 110. The reduction in the sensor line 110 pressure creates a corresponding variation in the amplitude of the sensor output signal provided to the comparator 118. When the amplitude of the sensor output signal exceeds the amplitude of the threshold signal from the foot pedal 126 the comparator 124 provides an output signal that opens the control valve 114.

The opened control valve allows fluid to flow into the sensor 110 line, through the check valve 112 and into the aspiration line 102 to increase the pressure within the line 102. The instantaneous flow of fluid through the open control valve 114 will increase the pressure within the sensor line 110 and vary the output of the pressure sensor 108 so that it no longer exceeds the threshold voltage. The polarity of the output signal from the comparator 118 reverses and closes the control valve 114. The pressure within the sensor line 110 drops until the comparator again provides an output signal that opens the control valve 114. This cycle is repeated until the steady state output signal of the pressure sensor no longer exceeds the threshold voltage. The control circuit 116 may include a timer circuit 128 that opens the control valve 114 and resets the system to the initial condition if the comparator 118 does not provide an valve open output signal for a predetermined time interval.

The threshold signal may have a preset value that defines a preset vacuum pressure. The surgeon can vary vacuum pressure of the aspiration line 102 by manipulating the foot pedal 126 and varying the amplitude of the threshold signal provided to the comparator 118. The system can be configured to operate in a "vacuum up" mode or a "vacuum down" mode. In the vacuum down mode depressing the foot pedal 126 will increase the power to the handpiece 104 and lower the pressure within the aspiration line 102. In the vacuum up mode depressing the foot pedal will increase the power to the handpiece 104 and increase the pressure within the line 102. The vacuum up mode can be enabled by inverting the threshold signal provided to the comparator 118. The modes can be switched through a switch or button (not shown).

The present invention provides a system that allows a surgeon to control the power to the handpiece and the vacuum pressure of the aspiration system through a single foot pedal 126. This reduces the complexity of operating the system. Additionally, the check valve 112 essentially seals the pressure sensor 108 so that the sensor 108 does not have to be sterilized after each procedure.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An aspiration system for a medical device, comprising:
   an aspiration line that has a vacuum pressure;
   a pressure sensor that senses the vacuum pressure;
   a sensor line that provides fluid communication between said pressure sensor and said aspiration line;
   a one-way check valve that is connected to said sensor line and located between said pressure sensor and said aspiration line, said one-way check valve allows fluid flow from said sensor line to said aspiration line and prevents fluid flow from said aspiration line to said sensor line;
   a control valve that provides a flow of fluid into said sensor line; and, a control circuit that is connected to said pressure sensor and controls said control valve.

2. The aspiration system as recited in claim 1, wherein said control circuit includes a comparator that has a first input which receives a sensor output signal, a second input which receives a threshold signal and an output that provides a control output signal to said control valve.

3. The aspiration system as recited in claim 2, wherein said second input is coupled to a foot pedal.

4. The aspiration system as recited in claim 3, wherein said threshold signal provided to said second input increases when said foot pedal is depressed.

5. The aspiration system as recited in claim 3, wherein said threshold signal provided to said second input decreases when said foot pedal is depressed.

6. The aspiration system as recited in claim 2, wherein said control circuit includes a timer circuit that is connected to said comparator and said control valve to open said control valve when said comparator does not provide said control output signal for a predetermined time interval.

7. A medical system, comprising;
    a handpiece;
    a foot pedal that can be depressed to generate and vary a threshold signal that controls a power of said handpiece;
    an aspiration line that has a vacuum pressure;
    a pressure sensor that senses the vacuum pressure and generates a sensor output signal;
    a control valve that can control the vacuum pressure within said aspiration line; and,
    a control circuit that compares said threshold signal with said sensor output signal and generates a control output signal to control said control valve.

8. The medical system as recited in claim 7, wherein said control circuit includes a comparator that has a first input that receives said pressure output signal, a second input that receives said threshold signal and an output that provides said control output signal.

9. The medical system as recited in claim 7, wherein said control circuit inverts said threshold signal.

10. The medical system as recited in claim 7, wherein said control circuit includes a timer circuit that is connected to said comparator and said control valve to open said control valve when said comparator does not provide said control output signal for a predetermined time interval.

11. The medical system as recited in claim 7, wherein said threshold signal increases when said foot pedal is depressed.

12. The medical system as recited in claim 7, wherein said threshold signal decreases when said foot pedal is depressed.

13. A method for controlling a vacuum pressure of an irrigation system used in conjunction with a handpiece, comprising:
    depressing a foot pedal to generate and vary a threshold signal to control a power of a handpiece;
    generating a sensor output signal that corresponds to a vacuum pressure of an aspiration line;
    comparing said threshold signal with said sensor output signal; and,
    generating a control output signal to open a control valve that allows fluid to flow into said aspiration line when said sensor output signal exceeds said threshold signal.

14. The method of claim 13, opening said control valve when said control output signal is not generated within a predetermined time interval.

15. A method for controlling a medial aspiration system, comprising:
    sensing a pressure of an aspiration line through a sensor line that is coupled to the aspiration line by a one-way check valve;
    opening a control valve to allow fluid to flow from a positive pressure source to the sensor line, and from the sensor line to the aspiration line through the one-way check valve, the one-way check valve closing when a pressure within the aspiration line is essentially equal to a pressure within the sensor line.

16. The method as recited in claim 15, further comprising comparing a sensor output signal that corresponds to the aspiration line pressure with a threshold signal, and opening the control valve when the sensor output signal exceeds the threshold signal.

17. The method as recited in claim 16, further comprising depressing a foot pedal to vary the threshold signal.

* * * * *